US011998280B2

(12) United States Patent
Chav et al.

(10) Patent No.: US 11,998,280 B2
(45) Date of Patent: *Jun. 4, 2024

(54) PATIENT-SPECIFIC INSTRUMENTATION FOR IMPLANT REVISION SURGERY

(71) Applicant: ORTHOSOFT ULC, Montreal (CA)

(72) Inventors: Ramnada Chav, Laval (CA); Jean-Sebastien Merette, Mont-St-Hilaire (CA); Tin Nguyen, Laval (CA); Karine Duval, Montreal (CA); Pierre Couture, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,233

(22) Filed: Jan. 13, 2023

(65) Prior Publication Data

US 2023/0172667 A1 Jun. 8, 2023

Related U.S. Application Data

(63) Continuation of application No. 16/217,680, filed on Dec. 12, 2018, now Pat. No. 11,576,725.

(Continued)

(51) Int. Cl.
 *A61B 34/10* (2016.01)
 *A61B 6/12* (2006.01)
 (Continued)

(52) U.S. Cl.
 CPC ............... *A61B 34/10* (2016.02); *A61B 6/12* (2013.01); *A61B 17/155* (2013.01);
 (Continued)

(58) Field of Classification Search
 CPC ....... G06T 2219/2021; G06T 2219/012; G06T 2210/41; G06T 2200/08; G06T 2200/04;
 (Continued)

(56) References Cited

U.S. PATENT DOCUMENTS

| | | | |
|---|---|---|---|
| 4,841,975 A | 6/1989 | Woolson | |
| 5,002,545 A | 3/1991 | Whiteside | |

(Continued)

FOREIGN PATENT DOCUMENTS

| | | |
|---|---|---|
| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Sing-Wai Wu
(74) *Attorney, Agent, or Firm* — NORTON ROSE FULBRIGHT CANADA LLP

(57) ABSTRACT

A system for creating at least one model of a bone and implanted implant comprises a processing unit; and a non-transitory computer-readable memory communicatively coupled to the processing unit and comprising computer-readable program instructions executable by the processing unit for: obtaining at least one image of at least part of a bone and of an implanted implant on the bone, the at least one image being patient specific, obtaining a virtual model of the implanted implant using an identity of the implanted implant, overlaying the virtual model of the implanted implant on the at least one image to determine a relative orientation of the implanted implant relative to the bone in the at least one image, and generating and outputting a current bone and implant model using the at least one image, the virtual model of the implanted implant and the overlaying.

14 Claims, 17 Drawing Sheets

Related U.S. Application Data

(60) Provisional application No. 62/597,670, filed on Dec. 12, 2017.

(51) Int. Cl.
*A61B 17/15* (2006.01)
*G06T 17/00* (2006.01)
*G06T 19/20* (2011.01)
*A61B 17/56* (2006.01)

(52) U.S. Cl.
CPC .......... *A61B 17/157* (2013.01); *G06T 17/00* (2013.01); *G06T 19/20* (2013.01); *A61B 2017/568* (2013.01); *A61B 2034/104* (2016.02); *A61B 2034/105* (2016.02); *A61B 2034/107* (2016.02); *A61B 2034/108* (2016.02); *G06T 2200/04* (2013.01); *G06T 2200/08* (2013.01); *G06T 2210/41* (2013.01); *G06T 2219/012* (2013.01); *G06T 2219/2021* (2013.01)

(58) Field of Classification Search
CPC ......... G06T 19/20; G06T 17/00; A61B 34/10; A61B 6/12; A61B 2034/104; A61B 2034/105; A61B 2034/107; A61B 2034/108
See application file for complete search history.

(56) References Cited

U.S. PATENT DOCUMENTS

| | | |
|---|---|---|
| 5,098,383 A | 3/1992 | Hemmy et al. |
| 5,490,854 A | 2/1996 | Fisher et al. |
| 5,768,134 A | 6/1998 | Swaelens et al. |
| 5,871,018 A | 2/1999 | Delp et al. |
| 5,916,219 A | 6/1999 | Matsuno et al. |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 9,820,821 B2 | 11/2017 | Aram et al. |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0234461 A1 | 10/2005 | Burdulis et al. |
| 2005/0267584 A1 | 12/2005 | Burdulis et al. |
| 2006/0111722 A1 | 5/2006 | Bouadi |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |

(56) References Cited

U.S. PATENT DOCUMENTS

| | | |
|---|---|---|
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |

(56) References Cited

U.S. PATENT DOCUMENTS

| | | |
|---|---|---|
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2015/0216614 A1 | 8/2015 | Simon |
| 2016/0022370 A1 | 1/2016 | Pavlovskaia et al. |
| 2016/0331467 A1 | 11/2016 | Slamin et al. |
| 2017/0007331 A1 | 1/2017 | Couture |
| 2018/0014891 A1* | 1/2018 | Krebs ................... A61B 5/055 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |

(56) References Cited

FOREIGN PATENT DOCUMENTS

| | | | |
|---|---|---|---|
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |
| WO | 2017008032 A1 | 1/2017 |

OTHER PUBLICATIONS

Hofmann et al, "Natural-Knee II System", Intermedics Orthopedics, Austin, TX, 1995.

\* cited by examiner

PATIENT-SPECIFIC INSTRUMENTATION FOR IMPLANT REVISION SURGERY

FIELD OF THE INVENTION

The present application is a continuation of U.S. patent application Ser. No. 16/217,680, filed on Dec. 12, 2018, which claims the priority of U.S. Patent Application No. 62/597,670, filed on Dec. 12, 2017 and incorporated herein by reference.

FIELD OF THE DISCLOSURE

The present disclosure pertains to patient specific instrumentation (PSI) used in orthopedic surgery and, more particularly, to PSI used for implant revision, and to image-based bone modeling in the context of implant revision.

BACKGROUND

Implant revision surgery is a process by which an existing implant is removed to be replaced by a new implant. However, due to the bond between the implant to be removed and the bone, the bone is often damaged during implant removal. As a result, the subsequent positioning and installation of a replacement implant may lack precision due to damaged bone surfaces. For instance, in knee revision surgery, machining of the bone surfaces using conventional cutting blocks may lack precision. One possible cause is that conventional bone landmarks used for defining the orientation of the cutting block may be altered or removed during the removal of the implant.

Patient specific instrumentation (hereinafter "PSI") pertains to the creation of instruments that are made specifically for the patient. PSI are typically manufactured from data using imaging to model bone geometry. Therefore, PSI have surfaces that may contact the bone in a predictable way as such contact surfaces are specifically manufactured to match the surface of a bone of a given patient. It would therefore be desirable to use PSI technology in an implant revision process.

SUMMARY OF THE DISCLOSURE

It is an aim of the present disclosure to provide a method for creating a PSI jig for implant revision surgery.

It is a further aim of the present disclosure to provide a system for creating a PSI implant revision jig model.

Therefore, in accordance with a first embodiment of the present disclosure, there is provided a system for creating at least one model of a bone and implanted implant, comprising: a processing unit; and a non-transitory computer-readable memory communicatively coupled to the processing unit and comprising computer-readable program instructions executable by the processing unit for: obtaining at least one image of at least part of a bone and of an implanted implant on the bone, the at least one image being patient specific, obtaining a virtual model of the implanted implant using an identity of the implanted implant, overlaying the virtual model of the implanted implant on the at least one image to determine a relative orientation of the implanted implant relative to the bone in the at least one image, and generating and outputting a current bone and implant model using the at least one image, the virtual model of the implanted implant and the overlaying.

Further in accordance with the first embodiment, for instance, obtaining a virtual model of the implanted implant includes obtaining dimensional data for the implanted implant.

Still further in accordance with the first embodiment, for instance, sizing the at least one current bone and implant model includes using said dimensional data.

Still further in accordance with the first embodiment, for instance, obtaining a virtual model of the implanted implant includes obtaining orientation data for the implanted implant.

Still further in accordance with the first embodiment, for instance, obtaining orientation data for the implanted implant includes obtaining a frontal plane, a sagittal plane and/or a transverse plane of the implanted implant.

Still further in accordance with the first embodiment, for instance, determining a joint line for the current bone and implant model includes using said orientation data.

Still further in accordance with the first embodiment, for instance, determining at least one bone axis for the current bone and implant model includes using said orientation data.

Still further in accordance with the first embodiment, for instance, the at least one image of at least part of a bone includes two or more radiographic images of the bone, and obtaining at least one image of at least part of a bone includes generating a 3D bone model from the two or more radiographic images of the bone.

Still further in accordance with the first embodiment, for instance, obtaining a virtual model of the implanted implant using an identity of the implanted implant includes generating a 3D model of the implanted implant from the at least one image, and comparing dimensions of 3D model of the implanted implant to a database of implant geometries to recognize the identity of the implanted implant.

Still further in accordance with the first embodiment, for instance, obtaining a virtual model of the implanted implant using an identity of the implanted implant includes obtaining a 3D CAD model of the implanted implant.

Still further in accordance with the first embodiment, for instance, generating and outputting a current bone and implant model includes generating a model of a tibia with implanted implant at a knee and/or of a femur with implanted implant at the knee.

In accordance with a second embodiment of the present disclosure, there is provided a system for creating at least one model of a patient-specific instrumentation jig for implant revision, comprising: a processing unit; and a non-transitory computer-readable memory communicatively coupled to the processing unit and comprising computer-readable program instructions executable by the processing unit for: obtaining at least one image of at least part of a bone requiring implant revision and of a primary implant on the bone, the at least one image being patient specific, identifying at least one reference anchor surface on the bone from the at least one image of the bone, the reference anchor surface configured to receive at least one guide reference, obtaining a planned placement of an intramedullary rod in the bone, determining an implant abutment surface on the primary implant, and generating and outputting virtual jig models using at least the identified reference anchor surface, the planned placement of the intramedullary rod and the determined implant abutment surface, the virtual jig models having patient specific geometries for guiding an alteration in the bone for the planned placement of the intramedullary rod as a function of cooperation of the virtual jig models with the determined implant abutment surface and with the at least one guide reference.

Further in accordance with the second embodiment, for instance, generating and outputting virtual jig models includes generating and outputting a reference jig model using at least the identified reference anchor surface, and the determined implant abutment surface, the reference jig model having at least one contact surface corresponding to the determined implant abutment surface for complementary connection with the determined implant abutment surface, at least one guide interfacing portion configured to guide a planting of the at least one guide reference in the reference anchor surface, and a patient-specific geometry between the at least one contact surface and the at least one guide interfacing portion, so as to position and/or orient the at least guide interfacing portion relative to the at least one reference anchor surface.

Still further in accordance with the second embodiment, for instance, generating and outputting virtual jig models includes generating and outputting a revision jig model using at least the identified reference anchor surface, and the planned placement of the intramedullary rod, the revision jig model having at least one guide interfacing portion configured to be mounted to the at least one guide reference, a drill guide, and a patient-specific geometry between the drill guide and the at least one guide interfacing portion, so as to position and/or orient the drill guide relative to the at least one guide reference, the drill guide aligned with desired medullary canal.

Still further in accordance with the second embodiment, for instance, creating at least one model of a bone and primary implant includes using the at least one image being patient specific.

Still further in accordance with the second embodiment, for instance, creating at least one model of a bone and primary implant includes obtaining a virtual model of the primary implant using an identity of the primary implant, overlaying the virtual model of the implanted implant on the at least one image to determine a relative orientation of the primary implant relative to the bone in the at least one image, and generating and outputting a current bone and implant model using the at least one image, the virtual model of the primary implant and the overlaying.

Still further in accordance with the second embodiment, for instance, obtaining a virtual model of the primary implant includes obtaining dimensional data and/or orientation data for the primary implant.

Still further in accordance with the second embodiment, for instance, sizing the at least one current bone and implant model includes using said dimensional data and/or determining a joint line and/or at least one bone axis for the current bone and implant model using said orientation data.

Still further in accordance with the second embodiment, for instance, obtaining a virtual model of the primary implant using an identity of the primary implant includes generating a 3D model of the primary implant from the at least one image, and comparing dimensions of 3D model of the primary implant to a database of implant geometries to recognize the identity of the primary implant.

Still further in accordance with the second embodiment, for instance, generating and outputting virtual jig models includes generating virtual jig models for revision of a tibial knee implant and/or a femoral knee implant.

In accordance with yet another embodiment, a method for creating at least one model of a patient-specific instrumentation jig for implant revision using a processing system, comprising: obtaining at least one image of at least part of a bone requiring implant revision and of an implanted implant on the bone, the at least one image being patient specific; identifying at least one reference anchor surface on the bone from the at least one image of the bone, the reference anchor surface configured to receive at least one guide reference; obtaining a planned placement of an intramedullary rod in the bone; determining an implant abutment surface on the implanted implant; and generating and outputting at least one virtual reference jig model using at least the identified reference anchor surface, the planned placement of the intramedullary rod and the determined implant abutment surface, the reference jig model comprising at least one contact surface corresponding to the determined implant abutment surface for complementary connection with the determined implant abutment surface, at least one guide interfacing portion configured to guide a planting of the at least one guide reference in the reference anchor surface, and a patient-specific geometry between the at least one contact surface and the at least one guide interfacing portion, so as to position and/or orient the at least guide interfacing portion relative to the at least one reference anchor surface, for subsequently planting the at least one guide reference in the at least one reference anchor surface as identified when the at least one contact surface is complementarily connected with the determined implant abutment surface, for subsequently guiding an alteration in the bone for the planned placement of the intramedullary rod.

In accordance with yet another embodiment of the present disclosure, there is a method for creating at least one model of a bone and implant revision using a processing system, comprising: obtaining at least one image of at least part of a bone and of an implanted implant on the bone, the at least one image being patient specific; obtaining a virtual model of the implanted implant using an identity for the implanted implant; overlaying the virtual model of the implanted implant on the at least one image to determine the orientation of the implanted implant relative to the bone in the at least one image; and generating and outputting a current bone and implant model using the at least one image, the virtual model of the implanted implant and the overlaying.

The feature or features of one embodiment may be applied to other embodiments, even though not described or illustrated, unless expressly prohibited by this disclosure or the nature of the embodiments.

Some details associated with the present embodiments are described above and others are described below.

DESCRIPTION OF THE PREFERRED EMBODIMENTS

Figure 1A:
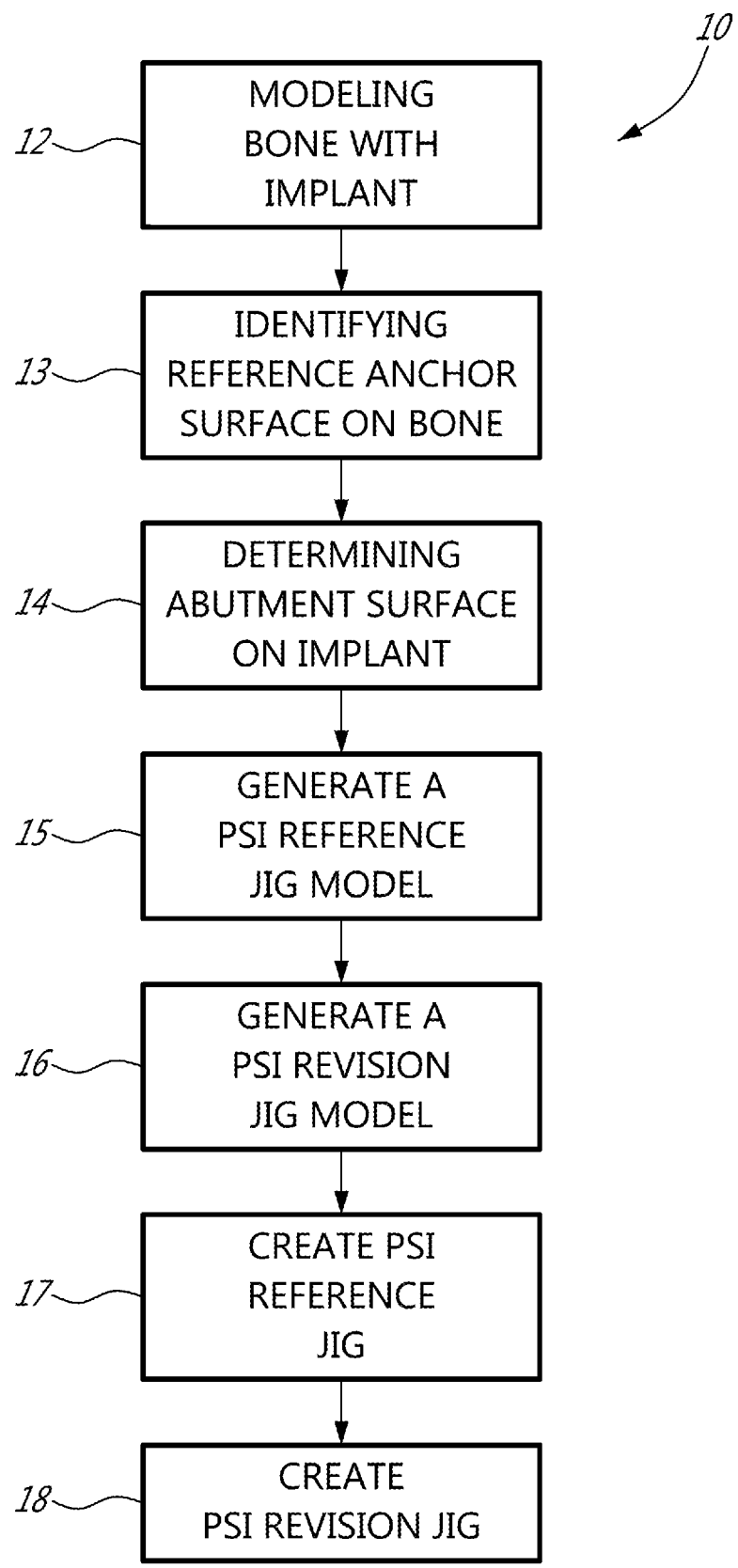
FIG. 1A is a flow chart showing a method for creating a PSI jig for implant revision in accordance with an embodiment of the present disclosure.

Referring to the drawings, and more particularly to FIG. 1A, there is illustrated a method 10 for creating patient specific instrumentation (hereinafter PSI) jigs for implant revision. For clarity, reference to patient specific in the present application pertains to the creation of negative corresponding surfaces, i.e., a surface that is the negative opposite of a patient bone/cartilage surface or implant, such that the patient specific surface conforms to the patient bone/cartilage surface or original implant, by complementary confirming contact. An instrument may also be patient specific in that it is used to plant guide references in a patient's bone, at a specific planned location based on the patient's specific anatomy—the geometry of the instrument is specific and unique to the patient. Such an instrument may not necessarily have a negative corresponding surface. The instrument may be fabricated specifically for a patient, for instance to have a cut plane positioned and oriented as a function of where pins or like landmarks will be in the bone, based on patient specific planning and bone imaging and/or modelling. The method is particularly suited to be used in knee revision in which the tibial knee implant, the femoral knee implant or both implants need to be replaced. The method may also be used in other orthopedic implant revision surgery, for instance in shoulder revision surgery. The expression "planning" refers to the pre-operative steps taken to prepare a surgery, before the surgery is commenced. For example, many planning steps, such as steps described herein, occur ahead of surgical day. It is conceivable to have some or all of the planning steps performed on surgical day as well.

Figure 1B:
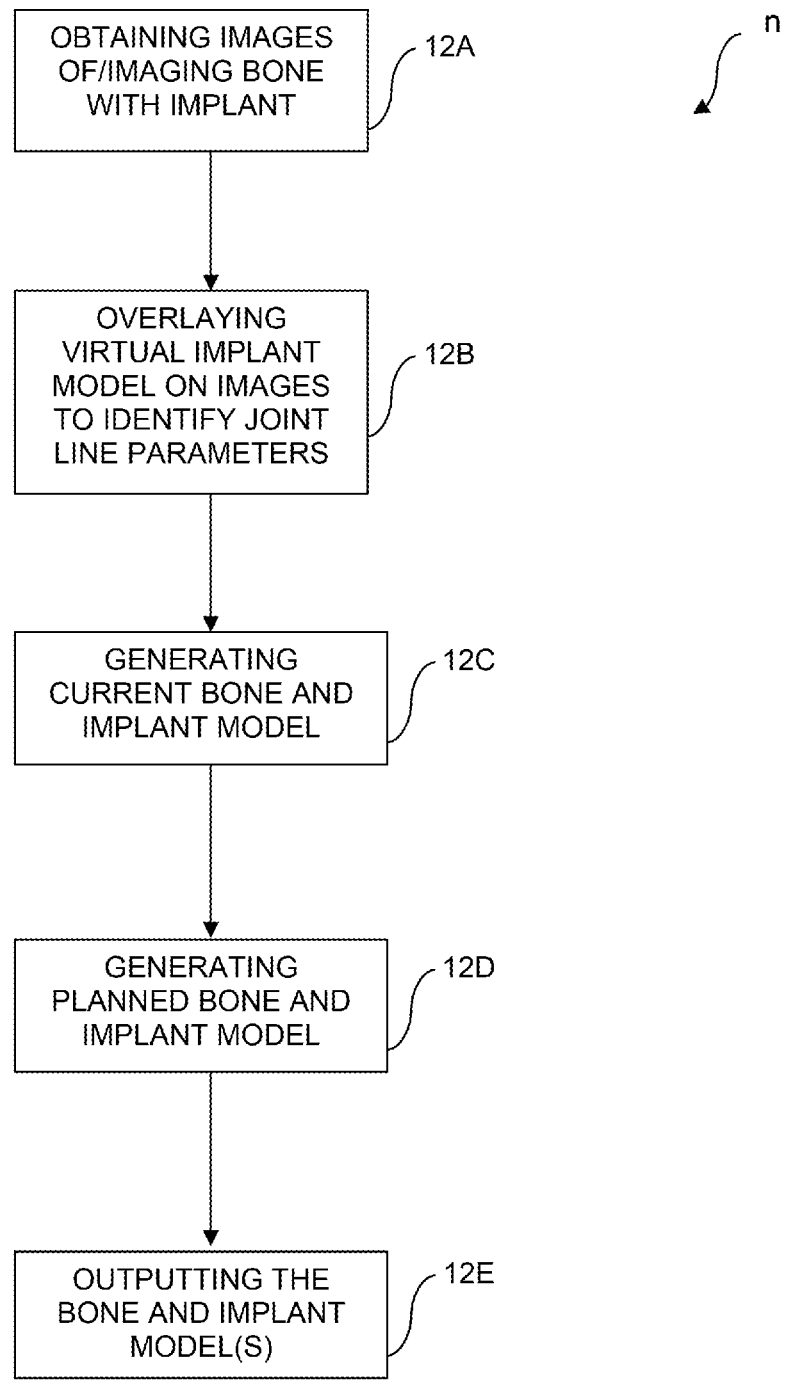
FIG. 1B is a flow chart showing a method for modelling a bone with implant in the method of FIG. 1A.
Figure 2A:
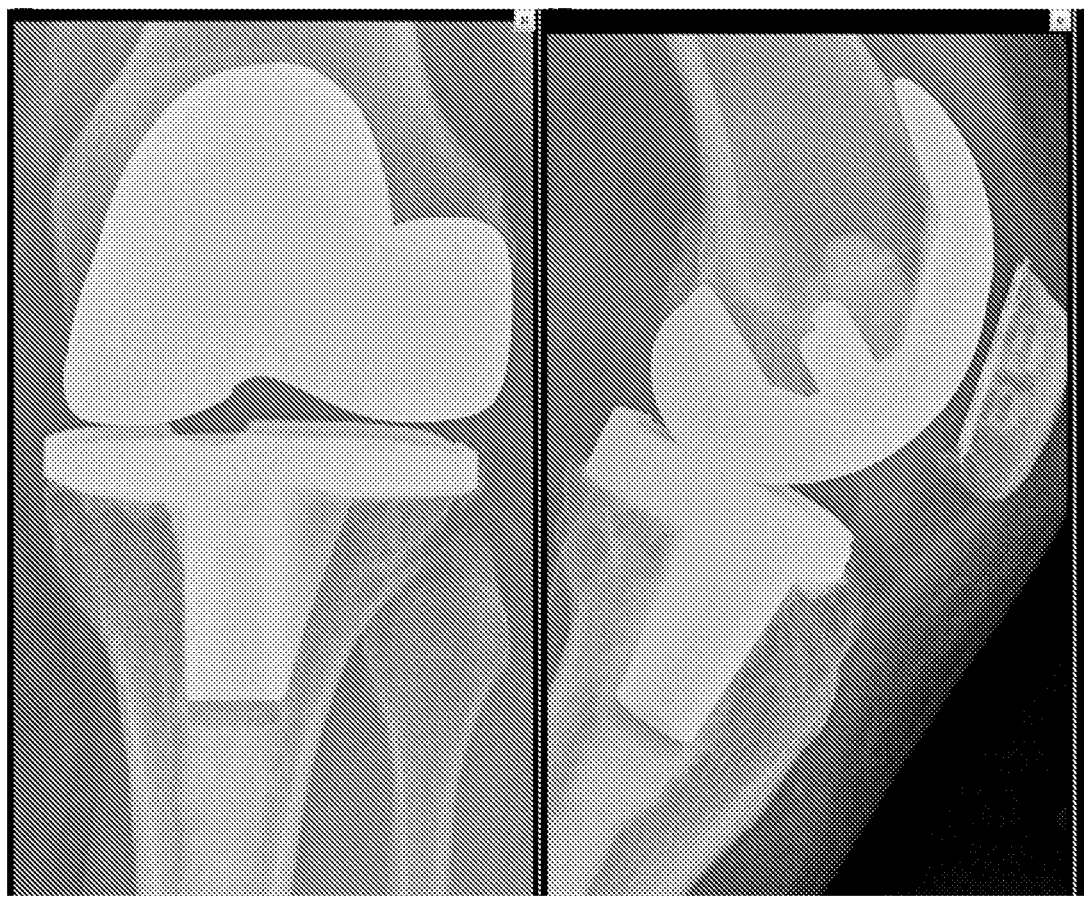
FIG. 2A is a display view of a bone and implant radiographic image with graphic calibration guides.

According to 12, the bone and its implant are modeled, in its current state and/or in a planned revision state. 12 may comprise numerous actions, as illustrated by 12A-12E in FIG. 1B. According to 12A, bone and implant images may be obtained and/or bone and implant may be imaged. The imaging may be done by any appropriate imaging technology such as CT scanning (computerized tomography), fluoroscopy, and/or like radiography methods, providing suitable resolution of images. In particular, as exemplified by FIG. 2A, both the bone and the implant in the image have a suitable resolution, contrast and definition if the imaging modality is radiography. Other imaging modalities are nonetheless considered, with subsequent work to obtain images of suitable resolution, contrast and definition. This includes magnetic resonance imagery (MRI) and scanning. As part of imaging or obtaining images in 12A, the entire bones may be imaged, and not only the joints, and multiple views can be obtained or imaged. For example, the point of view (POV) of the imaging equipment may be frontal and lateral.

Figure 2B:
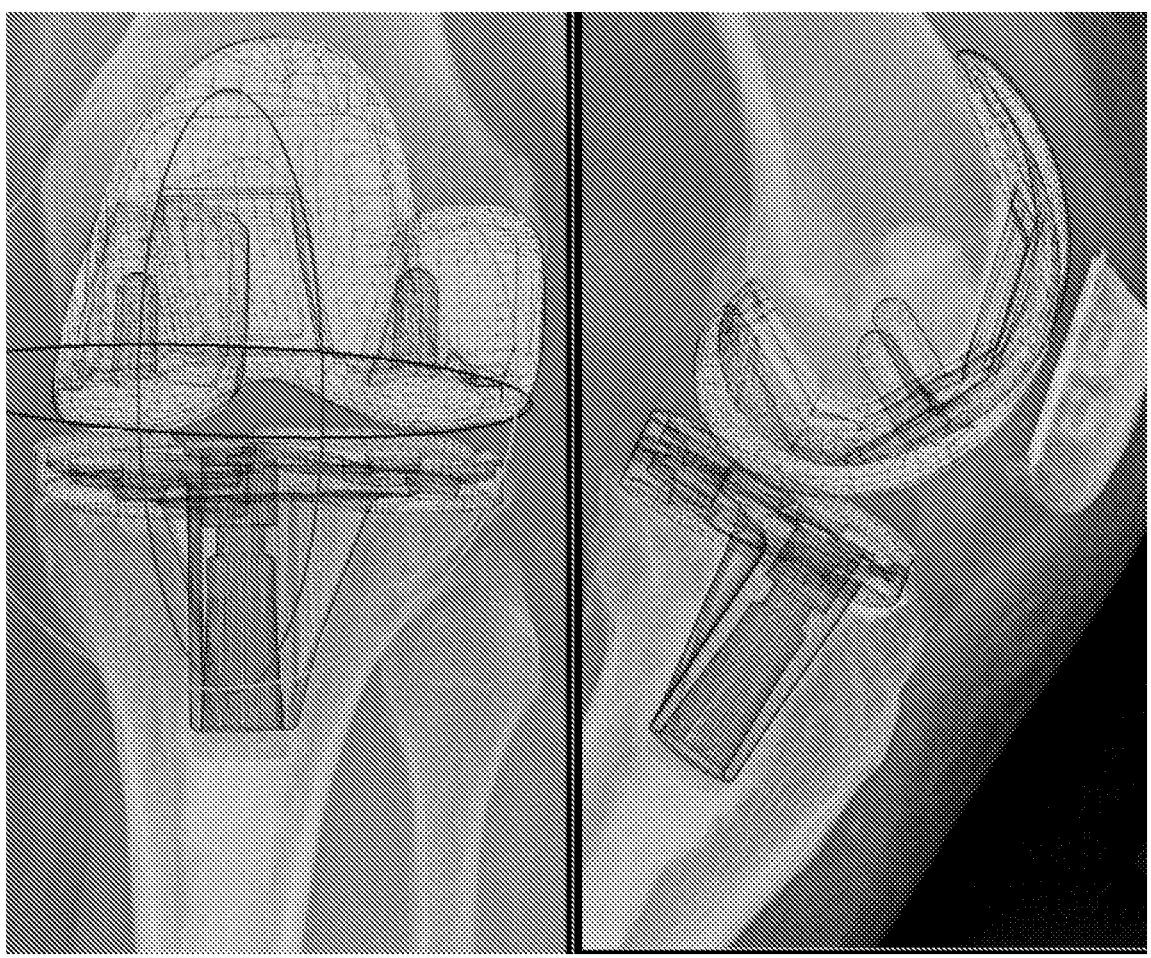
FIG. 2B is a display view of the bone and implant radiographic image of FIG. 2A with digital implant 3D model overlay and graphic calibration guides.

According to 12B, joint line parameters are identified from the images. According to an embodiment, the identification of the joint line parameters is achieved by using a digital implant 3D model as overlaid onto the image(s) of bone and implant of 12A, as shown in FIG. 2B. The digital implant 3D model may be obtained knowing the identity of the primary implant based on the patient file, by manual identification or automatic identification. With automatic identification, a CAS processor unit, such as described hereinafter, may for example access a library, database of implant geometries to recognize the primary implant and retrieve its digital 3D model. The expression "primary implant" is used consistently herein to identify the implant that is removed, whereas the expression "secondary implant" is used consistently herein to identify the implant that will replace the primary implant. The expression "implanted implant" may refer to both the primary implant and the secondary implant, when secured to the bone. Stated differently, the radiographic images may assist in performing a surface matching operation to merge the manufacturer's 3D virtual model of the implant with the bone imaging, if desired. With the primary implant brand/type/size, the CAD (computer-assisted design) 3D model of the primary implant is obtained. The 3D model may then be automatically registered with the image(s) of the bone and implant, such as the X-ray images. As part of the overlaying, a user or a processor unit may scale and/or rotate the digital implant 3D model relative to the image to achieve a precise overlay. In such a scenario, scaling entails that the implant 3D model maintains its shape (i.e., uniform scaling), the scaling of the implant being a modification of the projection of the implant by varying the implant CAD depth (between X-Ray source and detector). As the identity of the implant is known or may become known, the dimension of the bone may be calculated knowing the size of the implant. Stated differently, the implant 3D model whose dimensions are known (e.g., by knowing the identity and specifications), may be used as a magnification object to properly scale the bone, with scaling again being uniform scaling, involving a preservation of the shape, and geometric similarity of the bones and implant. In an embodiment, graphic calibration guides may be displayed in the overlaying process, and may be representative of the various orientations of the primary implant, i.e., frontal, sagittal and transverse planes of the primary implant. In FIG. 2B, the graphic calibration guides are in the form of circles, that appear as lines or ellipses depending on the POV. The orientations may be used in the calculation of joint line parameters, such as varus/valgus. Although 12A and 12B refer to a primary implant in the singular, the steps may be repeated for a second bone and second primary implant. For instance, in the example illustrated, both the tibial and femoral implant components may need revision, and thus the joint line parameter identification may entail performing the overlaying for both the tibia and the femur. The graphic images of FIG. 2B, with graphic calibration guide, may be optional, as the CAS processor unit and system described herein may proceed with the overlaying of 12B without an operator's input. The graphic calibration guide may also be present for visualization purposes, for a user to better observe the orientation of the primary implant(s).

Figure 2C:
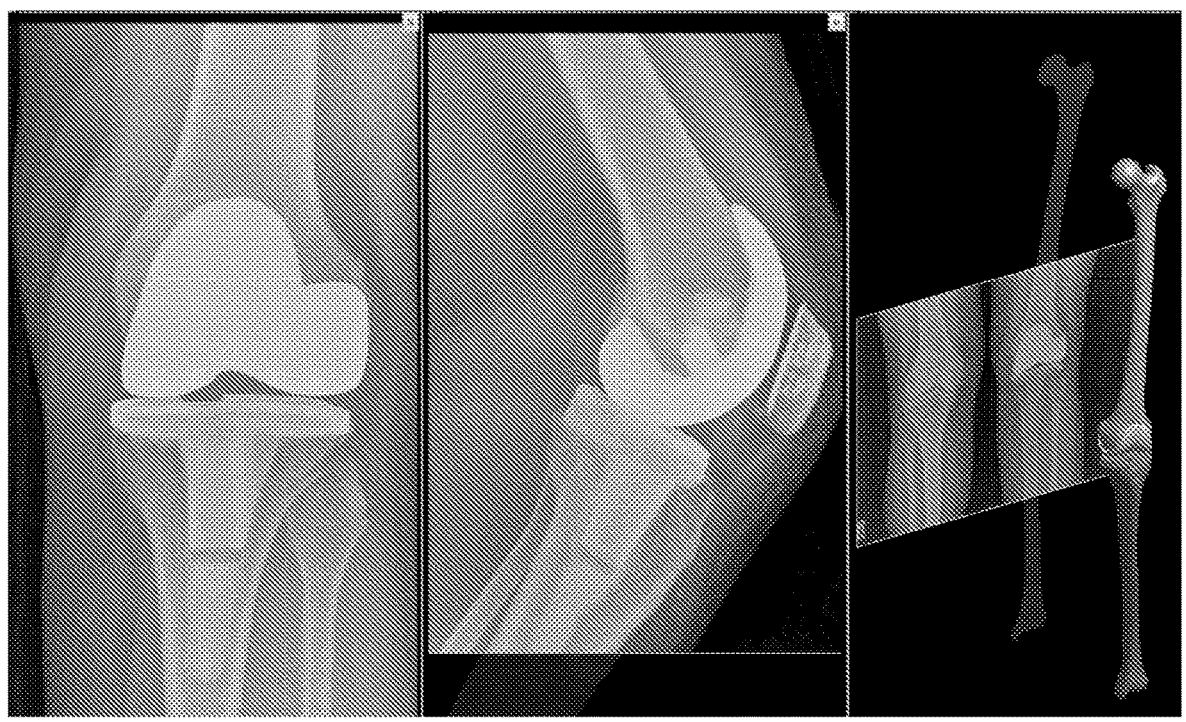
FIG. 2C is a display view of a current bone and implant three-dimensional (3D) model as generated in the method of FIG. 1B.

In 12C, the current bone and implant model may be generated. Stated differently, the bone in its current pre-revision condition may be modeled, and may integrate the 3D CAD implant model. The current bone and implant model may be in a virtual 3D format, as seen in FIG. 2C. The bone and implant model may have been previously obtained as part of 12A, or may be generated using the images of 12A. For example, the frontal and lateral images of the bone and implant may suffice in generating the current bone and implant model. As another possibility, the 3D bone model may have also been previously generated during the primary implant procedure, and thus the digital 3D bone model may be obtained and updated from the primary implant procedure. The model of the bone may have a surface geometry of parts of the bone that are exposed despite the presence of the implant and/or the limitations of the imaging. The model of the bone may include a surface geometry of the primary implant relative to adjacent bone surfaces, and a 3D geometry of the primary implant, for instance using a 3D model of implant (e.g., the CAD model from the manufacturer, etc), as overlaid in 12B. Therefore, the model of 12C includes orientation data for the primary implant, obtained for example from the planes of the primary implant. As described hereinafter, PSI jigs may directly abut against the primary implants being replaced, to position reference landmarks in the bone, whereby the orientation data of the implants contributes to the precision of the revision. It is also contemplated to abut the PSI jig against bone that is undamaged by implant removal, such as the tibia shaft the femur shaft, among other possibilities. According to an embodiment, the steps 12A-12C may be performed as part of a post-operative assessment of a procedure. For example, the leg may be imaged in the manner shown in the right-hand side panel of FIG. 2C, as an output or outcome of a post-operative imaging assessment.

The bone modeling may comprise generating a 3D surface of the bone (including just part of the bone, and not all of the bone) if the bone modeling is not directly performed by the imaging equipment, or if not complete. Again, in the instance in which multiple primary implants must be replaced (e.g., total knee revision), all bones supporting implants are modeled. Additional structures may be modeled as well, such as cartilage, hip joint, hip, ankle, etc. In addition to the joint line data of 12B, the current bone and implant model may also include a mechanical axis in the case of a femur and of a tibia, a femoral head center of rotation in the case of a femur, among available information.

Figure 2D:
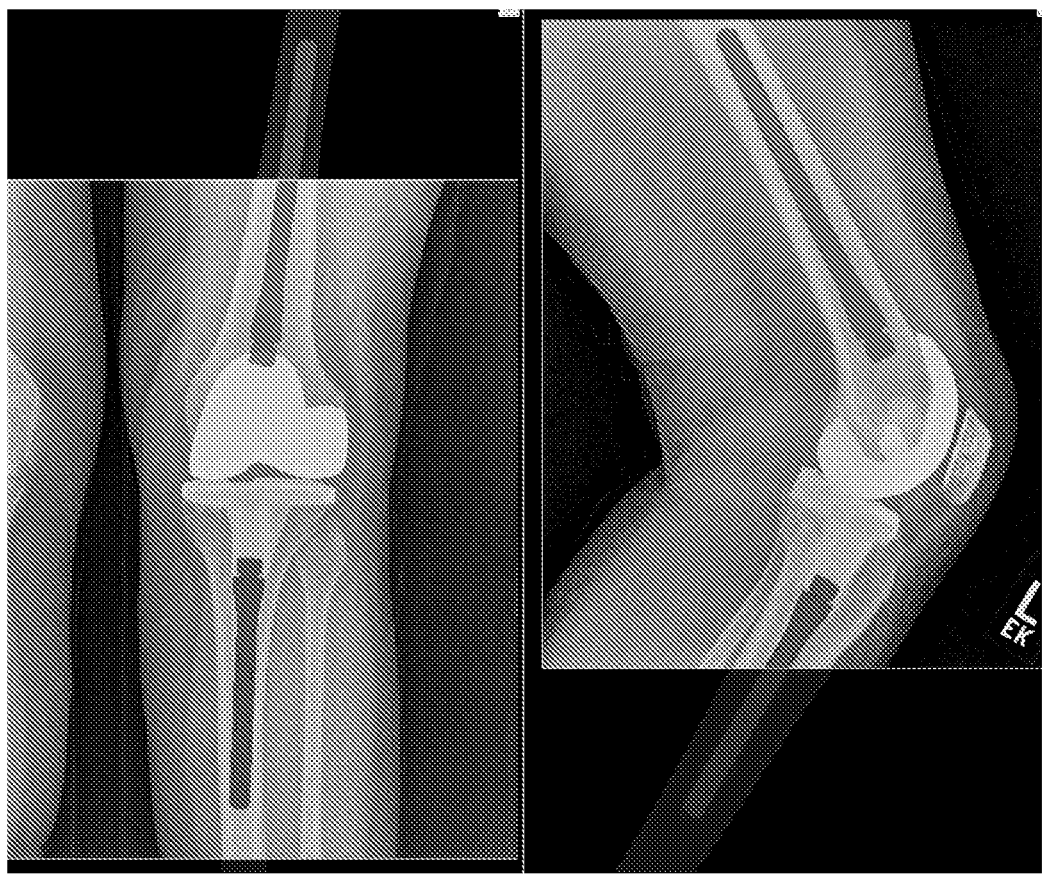
FIG. 2D is a display view of a planned bone and implant 3D model as generated in the method of FIG. 1B.
Figure 3:
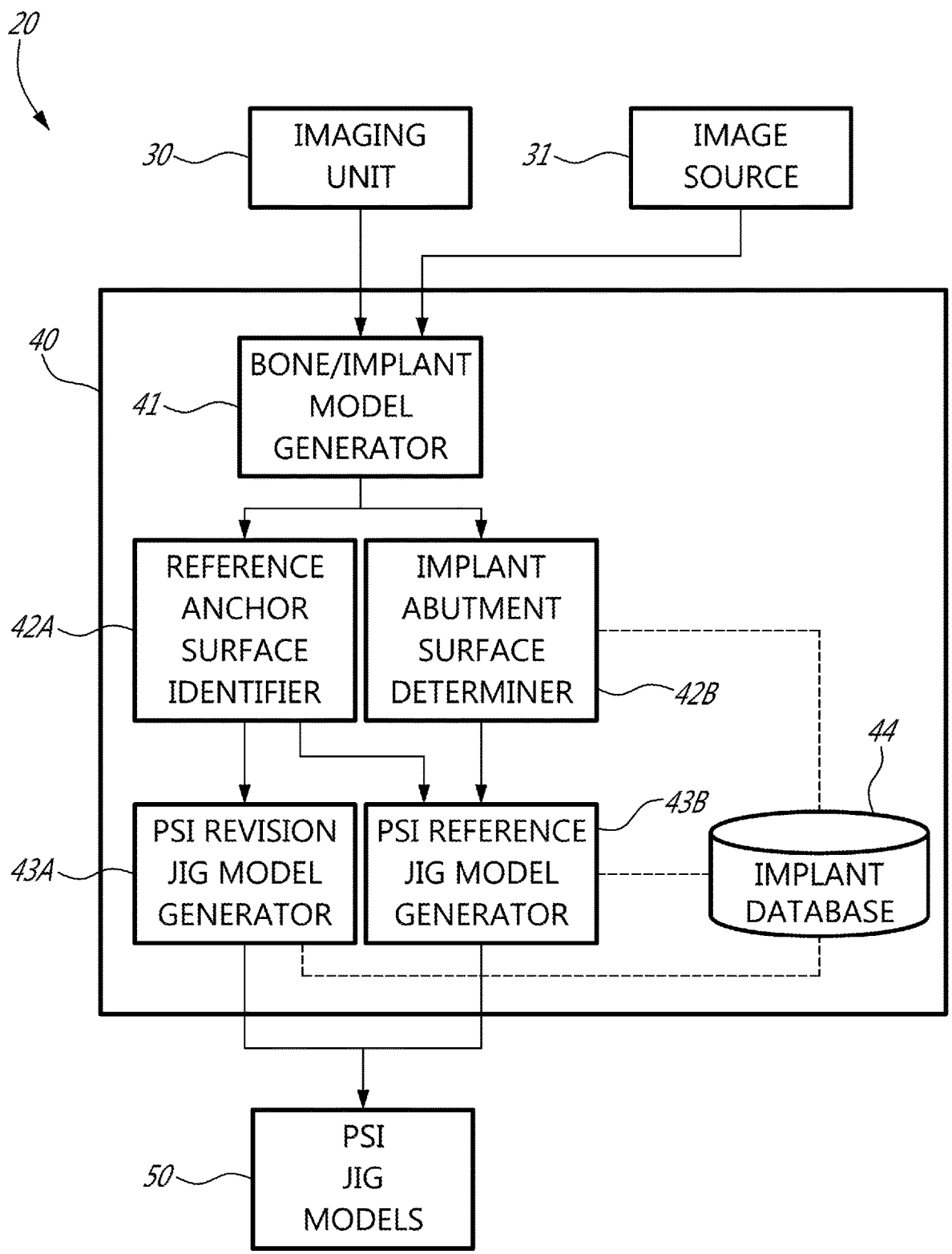
FIG. 3 is a block diagram showing a system for creating a PSI implant revision jig model in accordance with another embodiment of the present disclosure.

In 12D, the parameters of revision may be determined as part of revision planning. For example, a bone and revision implant planning model may be generated. The model of the bone and implanted primary implant and joint line parameters of 12B and 12C provides data that may be used by an operator, such as a surgeon, to plan revision surgery. In terms of planning, the operator may select the position and orientation of a 3D model of a secondary implant (i.e., a new implant, a replacement implant) that will be used in revision surgery by looking at the model and/or may determine locations for cut planes to support the replacement implant. As shown in FIG. 2D, the planning may be assisted by an overlay of the secondary implants on the bone models. Factors that may come into consideration include orientation in frontal, sagittal and axial plane, native joint line, primary implant joint line, bone damage, among other factors. Moreover, additional data such as a pre-operative kinematic analysis of the joint, and soft tissue tension, may be part of the data that may be available for the planning of the revision surgery, and may assist in determining a revised implant position and orientation.

It is common in revision surgery to implant intramedullary rods to reinforce the bones, as in shown in FIG. 2D. The planning may therefore including determining the precise type/length and placement of the intramedullary rods (i.e., orientation and/or position) relative to the mechanical axis, as well as the medullary cavity machining required for the bones to host the intramedullary rods (i.e., bone alteration models).

According to 12E, the bone and revision implant planning model may be output. The output may be in any appropriate form, including digital files and executable instructions. The bone and revision implant planning model may also have bone alteration models to receive the implants and other accessories (intramedullary rods) based on surgical planning. According to an embodiment, the bone and revision implant planning model are subsequently used in a virtual kinematic analysis of leg movement.

Referring back to FIG. 1A, according to 13, reference anchor surfaces are identified on the bone from the current model(s) of 12. The reference anchor surfaces may be selected as being sufficiently solid to support references such as pins or screws. The reference anchor surfaces may also or alternatively be selected as not being altered by the removal of the primary implant from the bone. For example, in the case of femoral knee revision, the reference anchor surfaces may be the medial epiphyseal bone, the anterior cortex and/or the femoral diaphysis. The epicondyles may be used to restore the joint line to set the axial position of the secondary implant. The axis may also be part of the jigs. Other parts of the femur may also be used as reference anchor surfaces.

As another example, in the case of tibial knee implant replacement, the reference anchor surfaces may be that of the medial and/or lateral aspects, and/or the superior tubercle portion of the tibia. In this case, the medial and/or lateral aspects may be used to restore the joint line by setting the axial position of the secondary implant. Other parts of the tibia may also be used as anchor surfaces. Similar considerations are taken into account in the case of shoulder surgery. In both cases, the anchor surfaces may be in close proximity to the primary implant (the implant already present, but to be removed in the revision process, also referred to as removed implant) as it is in the vicinity of the primary implant that bone alterations will be performed. Although the reference anchor surface(s) is in close proximity to the removed implant, the anchor surface will not substantially be damaged by the removal of the used implant.

In another embodiment, other factors influencing the selection of the reference anchor surface(s) are the planned location of the secondary implant, of the cut planes, and the geometry of stock/generic cutting blocks.

According to 14, an abutment surface on the primary implant is determined, for subsequent support of a PSI reference jig that is used to plant the guide references. As the primary implant has a known geometry—via the manufacturer's model and/or the modeling of 12—, the primary implant is an available support for a PSI instrument before it is removed. The primary implant not only has a known geometry, but also forms the joint surface of the articulation, whereby it may be a strategic PSI instrument support to ensure accuracy in reference placement.

The determination of the implant abutment surface takes into account the location of the guide reference(s), the implant abutment surface being for instance in relatively close proximity to the reference anchor surfaces. Other factors taken into consideration in the determination include any wear on the surface of implant, which worn implant surface may be avoided for PSI abutment to use instead unaltered parts of the implant, which unaltered parts would match the manufacturer's model of the implant. A negative-contour matching surface could hence be based directly on the manufacturer's 3D CAD model (or like 3D virtual model), for being applied against the primary implant.

According to 15, using the reference anchor surface(s) identified in 13, and the implant abutment surface(s) determined in 14, a PSI reference jig model is generated. The jig model will have a contact surface(s) defined to abut against the implant abutment surface(s) obtained in 14, in a predictable and precise manner. This may for example be the result of the use of the 3D CAD model of the primary implant. Moreover, the PSI reference jig model may have guiding features (e.g., guide holes) to guide an operator in anchoring the guide references in the bone, such that the guide references are at the planned position and orientation. The PSI reference jig model may also have a guiding feature to machine the medullary cavity for receiving intramedullary rods as planned.

In an embodiment, the PSI reference jig model is generated to enable the subsequent use of stock cutting jigs. In such a case, the PSI reference jig model is devised taking into consideration the geometry of the planned location of the secondary implant, of the cut planes, and the geometry of stock/generic cutting blocks. The PSI reference jig model may be in any appropriate format, such as an additive printing execution file or model, a numerical control machining file, etc.

According to 16, using the position and orientation of the guide references, the geometry of the secondary implant that is known (i.e., obtained from a database, from the manufacturer (e.g., 3D CAD model), generated as a PSI implant, etc), the intramedullary rod orientation and/or the reference anchor surfaces as obtained from the bone model(s), a PSI revision jig model may be generated. This may be as an alternative to using a stock/generic cutting jig. The jig model will have a guide interfacing portion adapted to be connected to the guide landmarks. The jig model may also have a contact surface(s) defined to abut against the reference anchor surface(s) obtained in 13, in a predictable and precise manner, with this contact surface not necessarily but possibly being a negative contour surface. In an embodiment, the PSI revision jig is a cutting block or cutting guide that will allow planes to be cut upon which will be anchored the implant. The PSI revision jig model of 16 may therefore define cutting planes, guides, slots, or any other tooling interface or tool, oriented and/or positioned to allow bone alterations to be formed in a desired location of the bone, relative to the contact surface(s). The PSI revision jig model may also take into consideration any revision planning done by the operator (e.g., surgeon), for example to allow the removal of sufficient bone material to reproduce desired gaps between cut planes on adjacent bones, etc. The PSI revision jig model may be in any appropriate format, such as an additive printing execution file or model, a numerical control machining file, etc.

According to 17, once the PSI reference jig model has been generated, the PSI reference jig may be created, with rapid prototyping, including numerical control machining, 3D printing or like additive printing, selective laser sintering, a combination thereof and/or any other suitable method. When installing the PSI reference jig on the primary implant bone, the contact surface(s) on the PSI jig is(are) applied against the corresponding implant abutment surface(s) of 14, with a unique complementary match that will ensure that the planned positioning is reached. The operator can then use the PSI reference jig to position the guide reference(s) in the reference anchor surface(s) as planned.

According to 18, once the PSI revision jig model has been generated, the PSI revision jig may be created, if such a PSI jig is used instead of a stock cutting jig. If the PSI revision jig is created, it may be done by rapid prototyping, including numerical control machining, 3D printing or like additive printing, selective laser sintering, a combination thereof and/or any other suitable method. When installing the PSI revision jig on the bone, virtually, the jig will be mounted onto the guide references (e.g., pins, screws), and therefore has another guide interfacing portion. It may also be desired that a contact surface(s) on the PSI revision jig is(are) applied against the anchor surface(s) of 13. The PSI jig created in 18 may then be used intra-operatively after the implant is removed to allow alterations to be made on the bone. For instance, in the case of total knee revision, jigs are used to perform femoral distal and tibial cuts.

While a specific order has been provided above, other orders are considered as well. For instance, it is contemplated to determine the abutment surface before identifying the reference anchor surfaces. Other step inversions are contemplated as well, for instance if a stock (i.e., non PSI) cutting jig is used.

Now that a method for creating a PSI reference jig and a PSI revision jig for implant replacement has been defined, a system is set forth.

A system for the creation of PSI jig models is generally shown at 20 in FIG. 2. The system 20 may comprise an imaging unit 30, such as a CT scan or an X-ray machine (e.g., with fluoroscopy), so as to obtain images of the bone and implant. This may also include MRI equipment. As an alternative, images may be obtained from an image source 31. As an example, a CT scan may be operated remotely from the system 20, whereby the system 20 may simply obtain images and/or processed bone and implant models from the image source 31.

The system 20 comprises a processor unit 40 (e.g., computer, laptop, with one or more processors, etc.) that comprises different modules so as to ultimately produce a jig model(s). A non-transitory computer-readable memory may be communicatively coupled to the processing unit 40 and have computer-readable program instructions executable by the processing unit for performing some or all of the actions of methods 10 and/or 12 of FIGS. 1A and 1B. The processing unit 40 of the system 20 may for example have a bone/implant model generator 41 receiving images from sources 30 or 31 to generate a 3D model of the bone with the implant, prior to implant revision. In accordance with the method 10 of FIGS. 1A and 1B, the 3D model of the bone with implant may comprise data pertaining to the surface geometry of a relevant portion of a bone and of the implant, including surfaces of the bone that are exposed despite the presence of the primary implant. The 3D model of the bone with implant may also include joint line information, full bone models with implants, mechanical axes, and/or center of rotations, etc. The 3D models may also include a bone and revision implant planning model with an identification of implants that may be used, and bone alteration models to receive the implants and other accessories (intramedullary rods) based on surgical planning.

The bone/implant model generator 41 will create the 3D model of the bone and implant that is then used by a reference anchor surface identifying module 42A and an implant abutment surface determining module 42B of the processing unit 40. Alternatively, the modules 42A and 42B may use a 3D model provided by the image source 31, provided the model obtained from the image source 31 comprises sufficient data. The virtual 3D model of the bone and implant may be generated using the manufacturer's CAD 3D model of the implant, whether it be via the image source 31 or via the bone/implant model generator 41.

The reference anchor surface identifier 42A identifies surfaces on the bone that may substantially not be altered by the removal of the damaged implant. The reference anchor surface(s) may be selected as being sufficiently solid to serve as support for guide landmarks such as pins or screws, etc. The reference anchor surface(s) may be selected as not obstructing the removal of the implant. For example, reference is made to step 13, in which examples are provided for appropriate reference anchor surfaces on the femur and the tibia in the case of total knee replacement. The reference anchor surface identifier 42A may identify the reference anchor surface using planned cut planes and/or planned replacement implant geometry and position and orientation, as well as stock cutting jig geometry. The reference anchor surface identifier 42A may use the 3D model of the bone and implant to achieve its function.

The implant abutment surface determining module 42B identifies abutment surfaces on the primary implant that will serve as support for a PSI reference jig, to plant the guide landmarks in the bone surfaces identified by the reference anchor surface identifier 42A. For example, reference is made to step 14, in which examples are provided for appropriate implant abutment surfaces. The implant abutment surface determining module 42B may provide target implant abutment surface(s) for the operator to participate in the selection. The implant abutment surface determining module 42B may use the 3D model of the bone and implant to achieve its function.

Once the reference anchor surface(s) is(are) identified and the implant abutment surface are determined, a PSI revision jig model generator module 43A may generate a revision jig model (unless a stock cutting jig is used). A PSI reference jig model generator module 43B may also generate a reference jig model. As in 16 and 17 of the method 10, the reference jig model will have a contact surface(s) defined to abut against the implant determined by the module 42B, in a predictable and precise manner, for the planting of guide references. The revision jig model will have a guide interfacing portion to be mounted to the guide references. The revision jig model may also be devised to contact the reference anchor surface. As the PSI revision jig will support a tool to perform alterations on the bone, the jig model comprises cutting planes, guides, slots, or any other tooling interface or tool, trackers, oriented and/or positioned to allow bone alterations to be formed in a desired location of the bone, relative to the contact surface(s).

Thus, jig model generator modules 43A and 43B may also take into consideration any revision planning done by the operator (e.g., surgeon). The jig model generator modules 43A and 43B may also take into consideration a geometry of the existing damaged primary implant, the secondary implant (e.g., obtained from an implant database 44), in addition to the anchor surface(s).

Accordingly, the system 20 outputs PSI jig model(s) 50 that will be used to create the PSI reference jig and optionally the PSI revision jig. The PSI reference jig serves to place the guide references while the PSI revision jig, or alternatively a stock cutting jig, is then used intra-operatively to resurface bone for subsequent implant installation, based on the positioning and path of the guide references, as described for method 10 in FIG. 1.

Exemplary embodiments are now provided, with a tibial application and a femoral application, among numerous other possibilities.

Referring concurrently to FIGS. 4-8, a knee portion of a tibia is generally shown at 60, with a primary implant 61, to be revised. A PSI reference jig 62 has a body 63 having a geometry specific to the patient. The PSI reference jig 62 may be used to space in a given position and orientation a PSI contact surface 64 from a guide interfacing portion 65, for instance as planned in the pre-planning. The geometry of the PSI reference jig 62 may be patient specific, in that the spacing between the PSI contact surface 64 and the a guide interfacing portion 65 is specific to a patient, according to the planning and image done beforehand. Hence, the guide references, shown as pins 66, are planted in the reference anchor surface, shown in the embodiment as the posterior face of the tibia 60. The anterior face of the tibia 60, the lateral face(s) of the tibia 60 could also or alternatively be used, as could other parts of the tibia 60. The PSI contact surface 64 of the jig 62 may abut against a tibial plateau portion of the implant 61 in a unique complementary manner. The PSI contact surface 64 of the jig 62 could also or alternatively abut against a periphery or contour of the implant 61. The PSI contact surface 64 of the jig 62 may also have PSI contact surfaces for abutment with the tibia 60, as observed.

Figure 4:
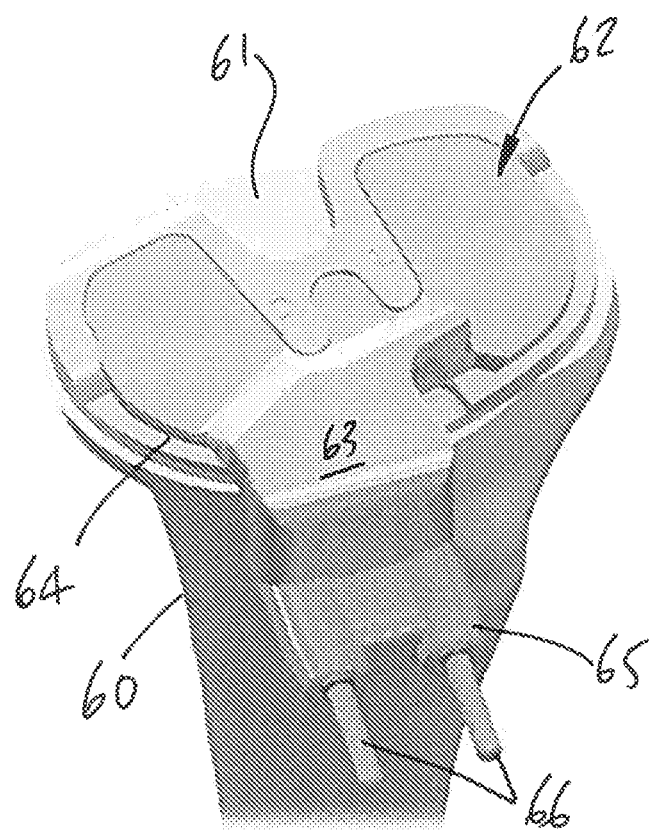
FIG. 4 is a perspective view of a tibia with a tibial PSI reference jig thereon, to plant guide landmarks.
Figure 5:
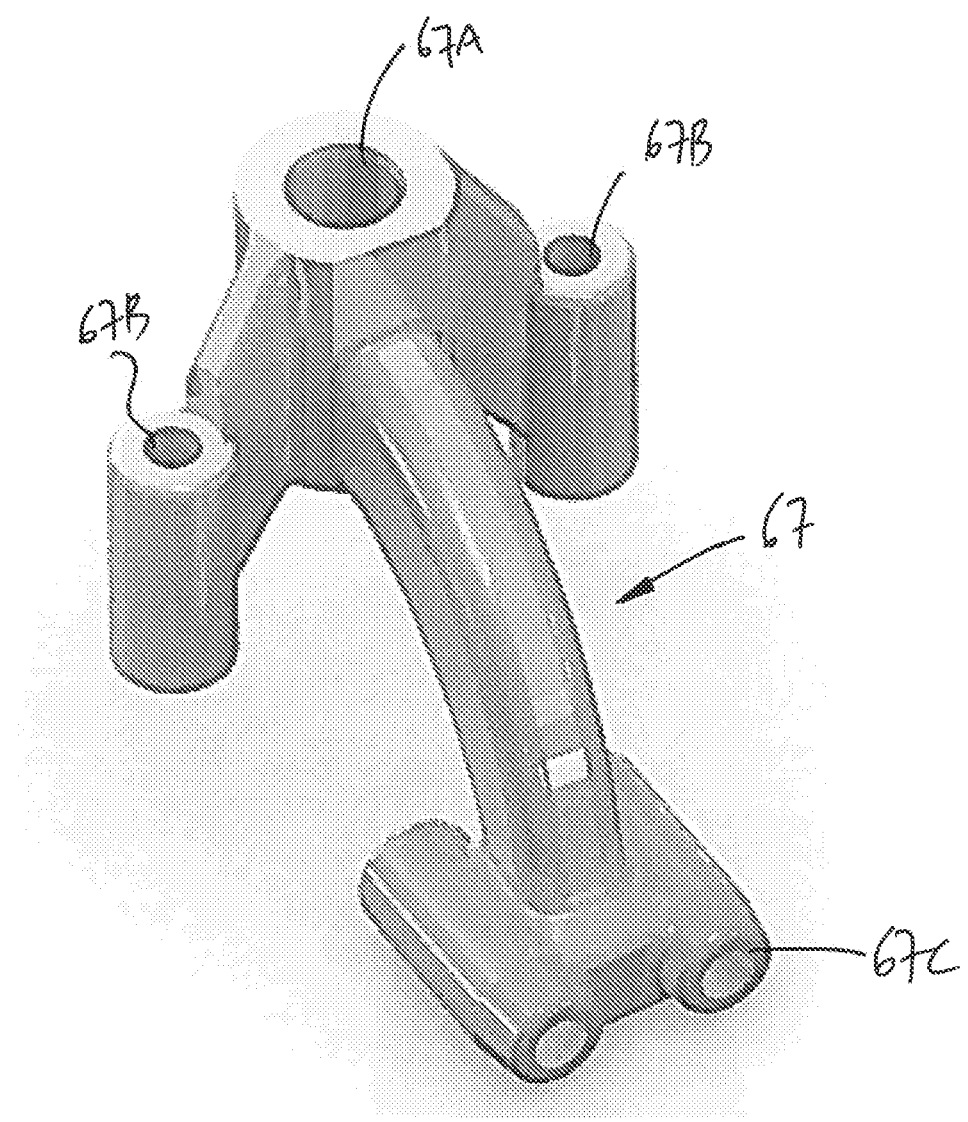
FIG. 5 is a perspective view of a tibial PSI revision jig in accordance with another embodiment of the present disclosure.
Figure 6:
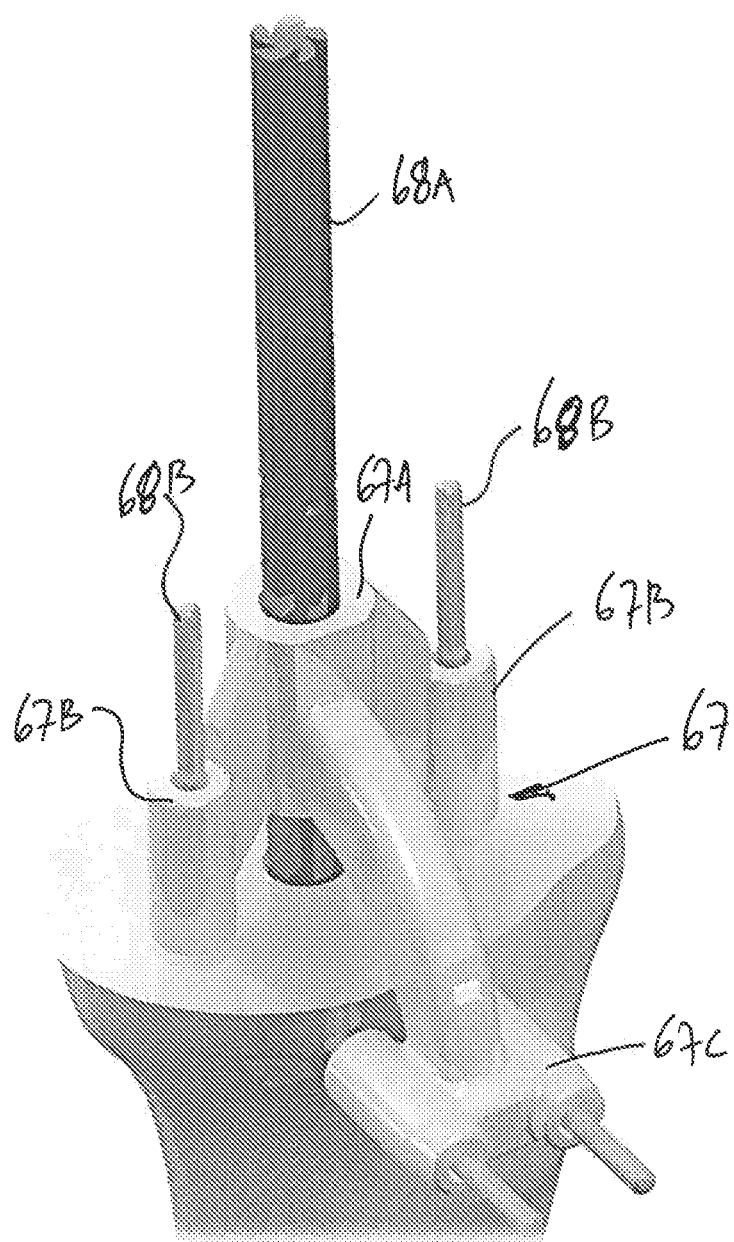
FIG. 6 is a perspective view of the tibia of FIG. 4, with the tibial PSI revision jig of FIG. 5 on the guide landmarks.
Figure 7:
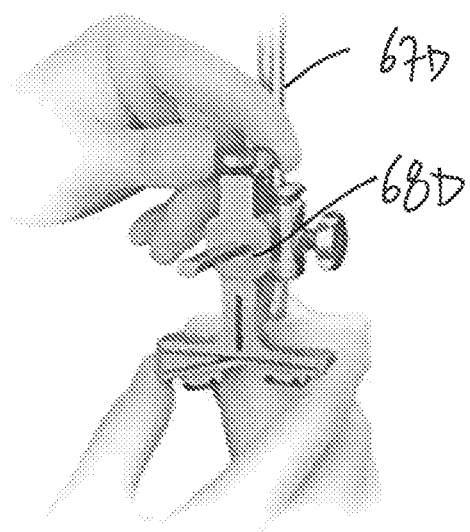
FIG. 7 is a perspective view of a tibial depth cut guide mounted to an intramedullary rod on the tibia of FIG. 5.

Once the guide reference pins 66 are planted at FIG. 4, the PSI reference jig 62 may be removed, leaving the pins 66 positioned and oriented as planned. As shown in FIGS. 5 and 6, the primary implant 61 may be removed, and the PSI revision jig 67 may be slid onto the pins 66. The jig 67 is shown as having a drill guide 67A and pin guides 67B. The drill guide 67A is oriented to guide an operator or robot in drilling with a drill bit 68A (e.g., step drill) the medullary cavity to an appropriate size, depth and orientation to receive an intramedullary rod, as planned. The pin guides 67B are used to drill holes or position pins 68B that will serve as stabilizers for the PSI revision jig 67 on the tibia, to ensure the drill guide 67A is rigidly anchored, for the intramedullary rod to be positioned as planned. The jig 67 may be patient specific by having a geometry to its body defined as a function of the patient's anatomy, for the guides 67A and 67B to be located based on the position of guide interfacing portion 67C (e.g., pin slots) interfacing with pins 66. A tibial depth cutting guide 68D may then be used as in FIG. 7. The cutting guide 68D is mounted for example on a guide rod 67D (or on the drill bit 68A) projecting out of the medullary cavity, after the drilling using the drill guide 67A. The tibial depth cutting guide 68D may consequently have a planned orientation because of its cooperation with the guide rod 67D or drill bit 68A. The tibial depth cutting guide 68D may then be pinned or screwed to the tibia. The guide rod 67D or drill bit 68A may then be removed for the cuts to be made.

Figure 8:
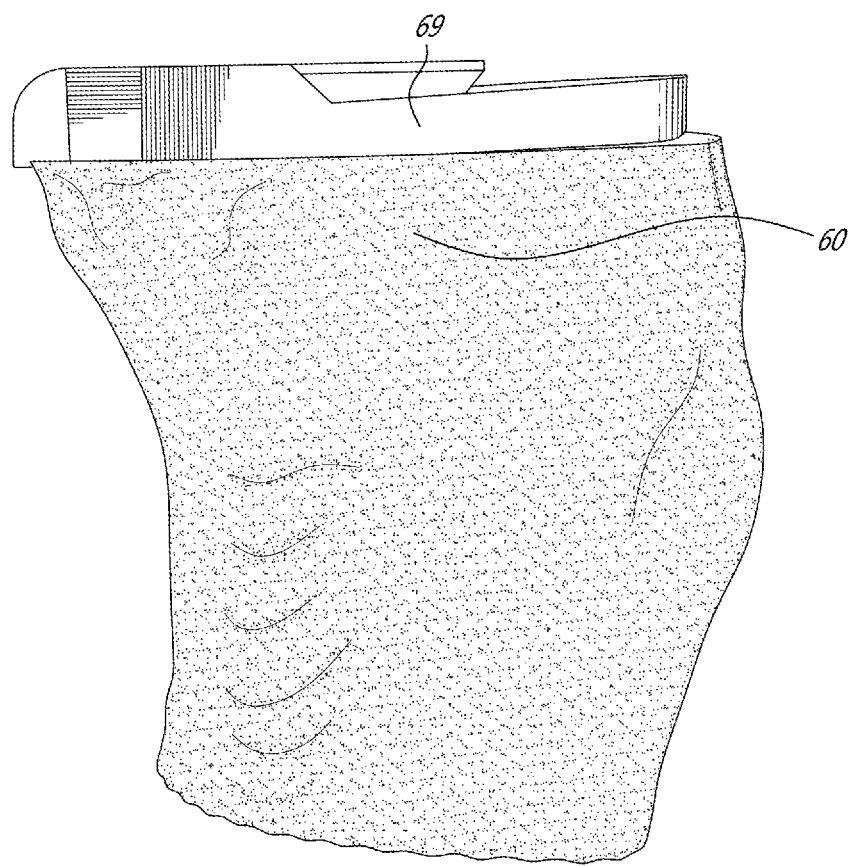
FIG. 8 is a perspective view of the tibia of FIG. 4, with a secondary implant after revision.

Referring to FIG. 8, once the cuts have been made using the jig 67 and the cutting guide 68D, and a secondary implant 69 may be installed. The secondary implant 69 may or may not include an intramedullary rod as in FIG. 2D.

Referring concurrently to FIGS. 9-13, a femur is generally shown at 70, at the knee joint, with an implanted implant 71, to be revised, i.e., a primary implant. A PSI reference jig 72 has a body 73 having a geometry specific to the patient, to position and orient a PSI contact surface 74 relative to a guide interfacing portion 75 based on pre-operative planning. Hence, the guide references, shown as pins 76A, are planted in the reference anchor surface, shown in the embodiment as the anterior face of the femur 70. The posterior face and/or the lateral face(s) of the femur 70 are options among others for the reference anchor surface of the femur 70. The PSI contact surface 74 of the jig 72 abuts against a distal end of the primary implant 71. The PSI contact surface 74 may or may not have PSI contact surfaces for abutment with the femur 70.

Figure 9:
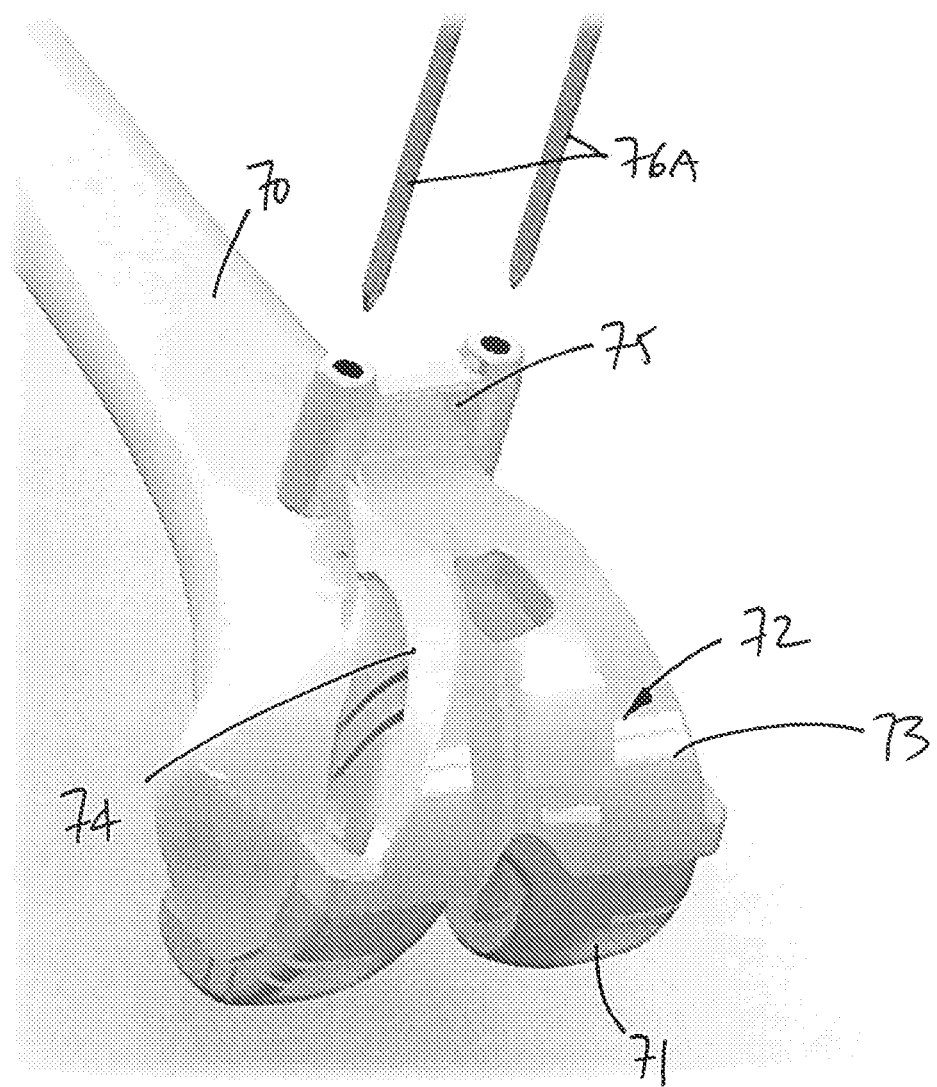
FIG. 9 is a perspective view of a femur with a femoral PSI reference jig thereon, to plant guide landmarks.
Figure 10:
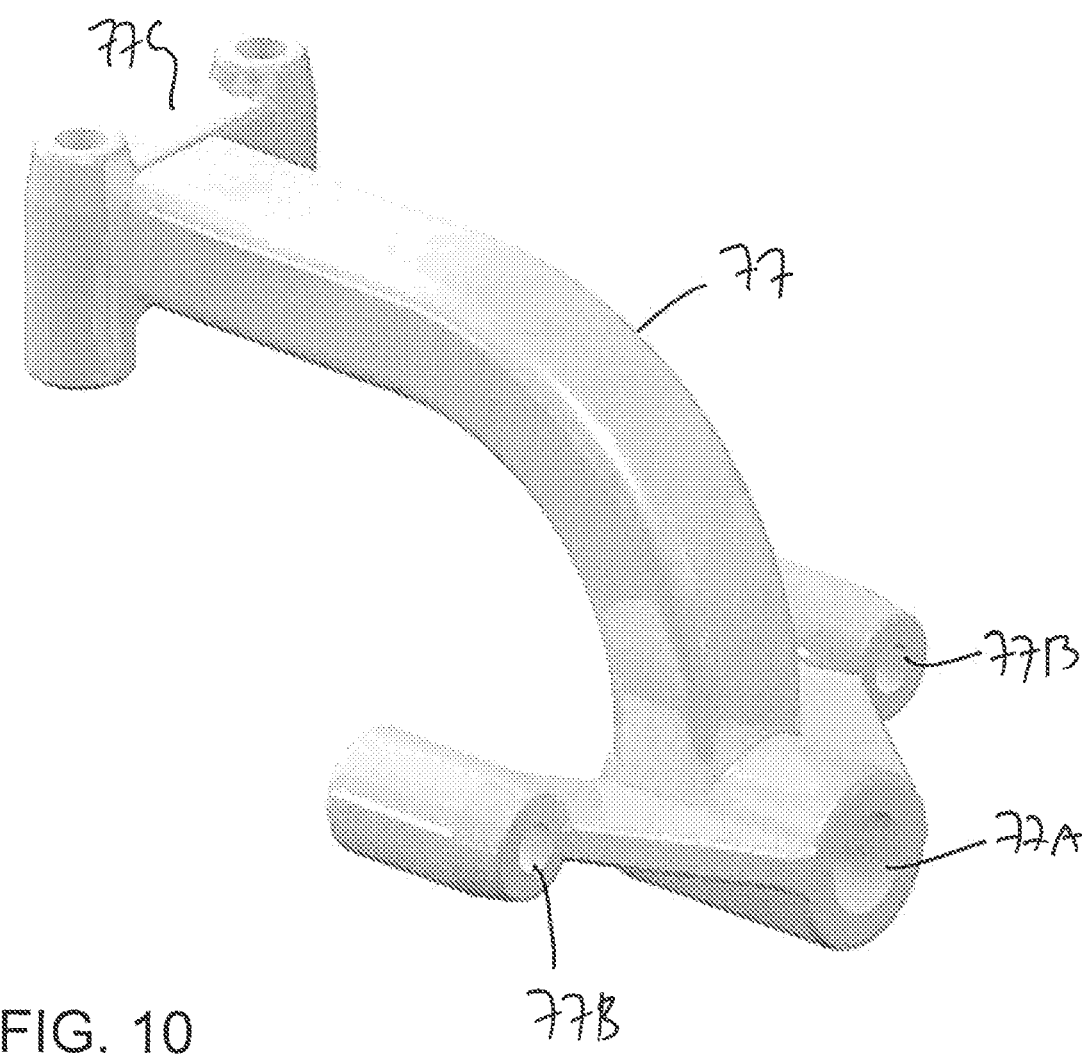
FIG. 10 is a perspective view of a femoral PSI revision jig in accordance with another embodiment of the present disclosure.
Figure 11:
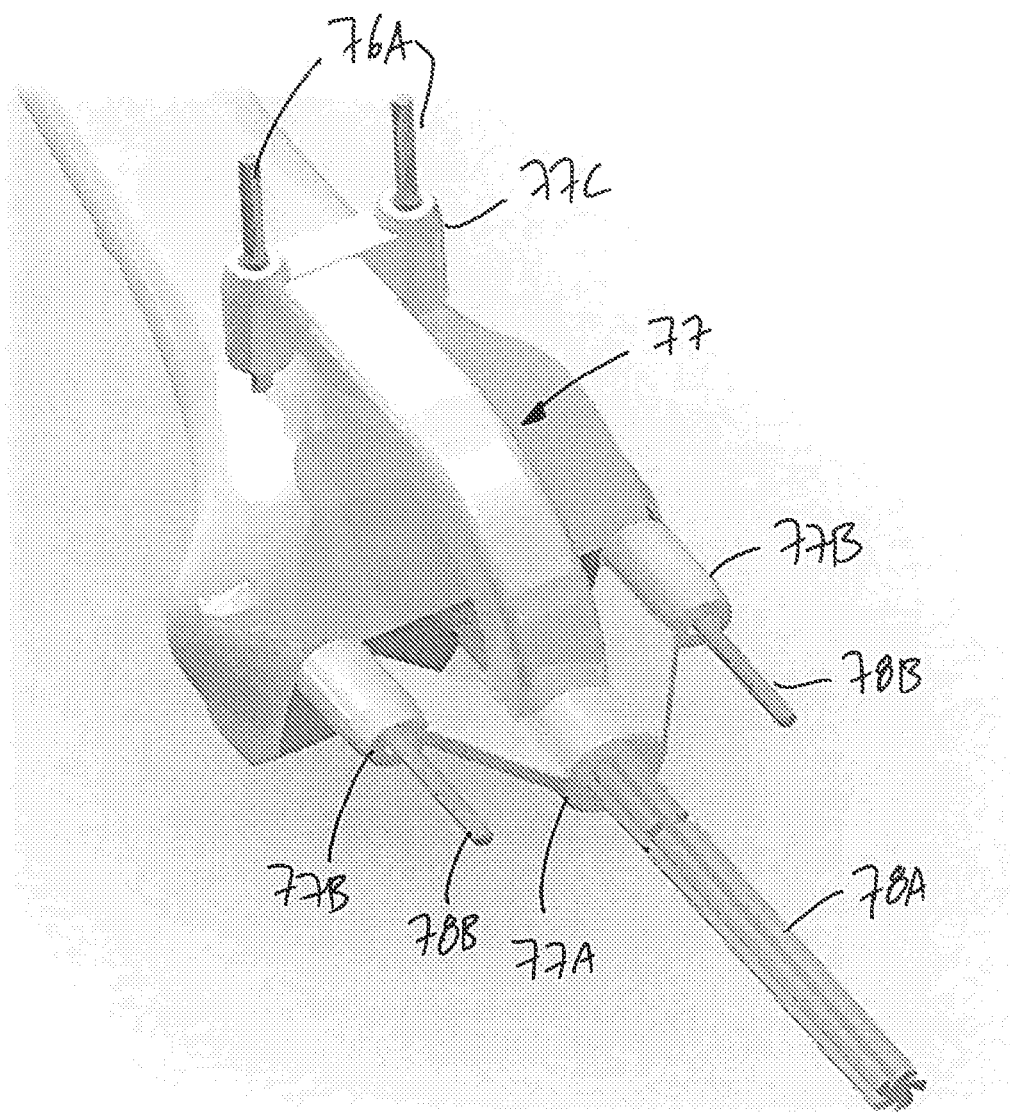
FIG. 11 is a perspective view of the femur of FIG. 9, with the tibial PSI revision jig on the guide landmarks.
Figure 12:
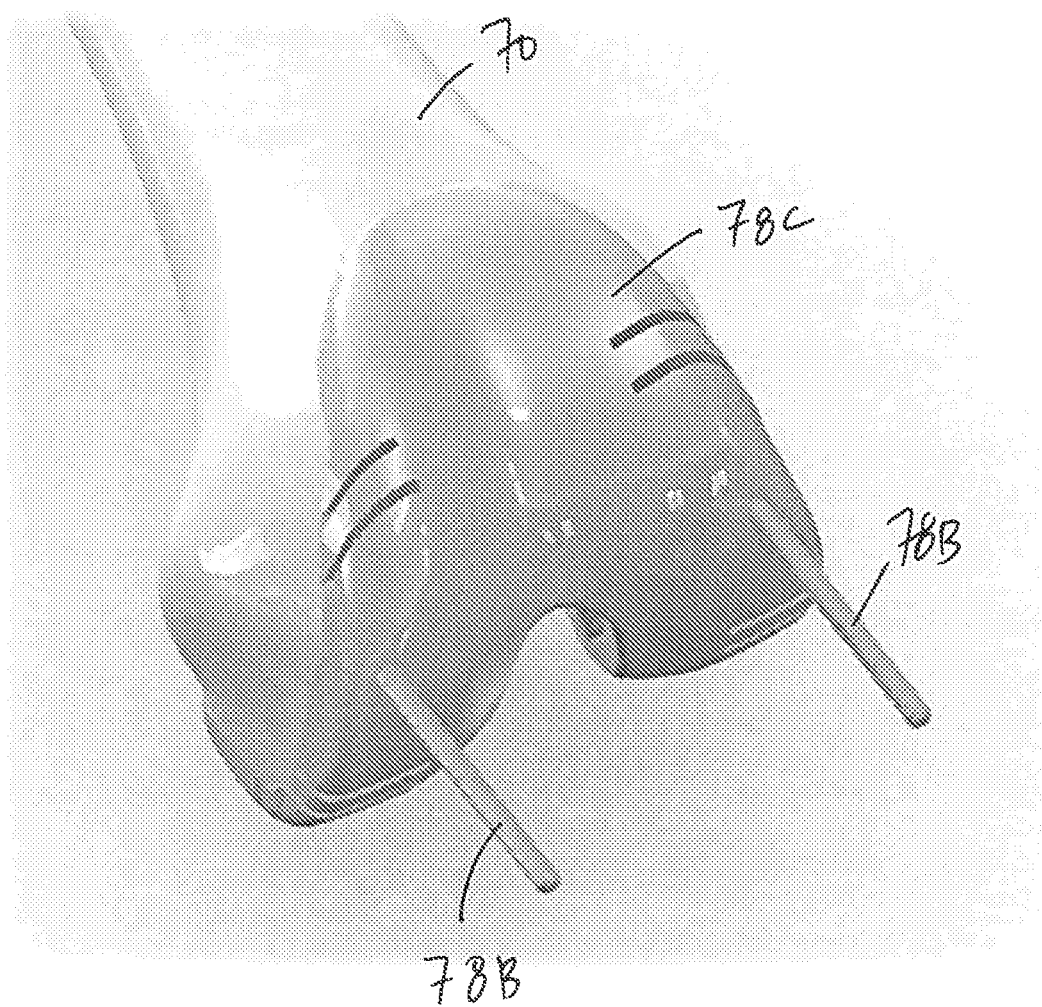
FIG. 12 is a perspective view of the femur of FIG. 9, with a cut guide on the guide landmarks.

Once the guide reference pins 76A are planted as in FIG. 9, the PSI reference jig 72 may be removed, leaving the pins 76A positioned and oriented as planned. As shown in FIGS. 10 and 11, the primary implant 71 may be removed. The PSI revision jig 77 may be slid onto the pins 76A. The jig 77 is shown as having a drill guide 77A and pin guides 77B. The drill guide 77A is oriented to guide an operator or robot in drilling with a drill bit 78A (e.g., step drill) the medullary cavity to an appropriate size, depth and orientation to receive an intramedullary rod, as planned. The pin guides 77B may optionally be used to position pins 78B that will serve as stabilizers to ensure that the PSI revision jig 77 is fixed to the femur during the use of the drill guide 77A with the drill bit 78A. The pin guides 77B may be used to optionally position trial components 78C on the bone as in FIG. 12, to effect soft tissue balancing. The jig 77 may be patient specific by having the geometry of its body defined as a function of the patient's anatomy, as planned according to FIG. 1B, for the guides 77A and 77B to be located based on the position of guide interfacing portion 77C. The pins 76A or 78B may then be used for a cutting guide sized as a function of the desired implant size. The implant size being determined from planning, and/or adjusted subsequent to the soft tissue balancing performed with the trial component 78C.

Figure 13:
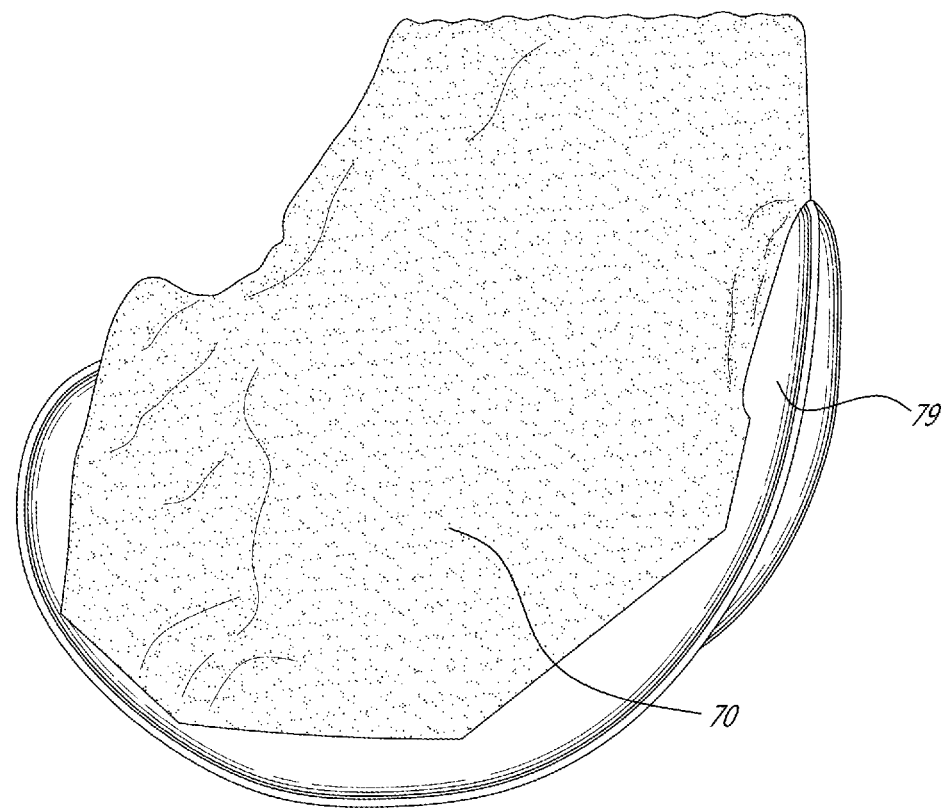
FIG. 13 is a perspective view of the femur of FIG. 9, with a secondary implant after revision.

Referring to FIG. 13, once the cuts have been made, a secondary implant 79 including or not an intramedullary rod may be installed.

It is considered to use the reference guides as guides for a robotic arm to cut the planes on the bone. In such a case, no revision jig model would be required. Instead, a navigation file could be provided for a robotic system to perform surgery based on the placement on the reference guides.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A system for guiding surgical alterations on a bone in revision surgery, comprising:
   a processing unit; and
   a non-transitory computer-readable memory communicatively coupled to the processing unit and comprising computer-readable program instructions executable by the processing unit for:
      obtaining at least one image of at least part of a bone and of an implanted implant on the bone, the at least one image being patient specific,
      obtaining a virtual model of the implanted implant using an identity of the implanted implant, the virtual model including orientation data for the implanted implant,
      overlaying the virtual model of the implanted implant on the at least one image to determine a relative orientation of the implanted implant relative to the bone in the at least one image,
      generating and outputting a current bone and implant model using the at least one image, the virtual model of the implanted implant and the overlaying, and
      guiding alterations in the bone using the current bone and implant model.

2. The system according to claim 1, wherein obtaining a virtual model of the implanted implant includes obtaining dimensional data for the implanted implant.

3. The system according to claim 2, further comprising sizing the at least one current bone and implant model using said dimensional data.

4. The system according to claim 1, wherein obtaining a virtual model of the implanted implant includes obtaining at least one axis of implanted implant.

5. The system according to claim 4, wherein obtaining orientation data for the implanted implant includes obtaining a frontal plane, a sagittal plane and/or a transverse plane of the implanted implant.

6. The system according to claim 4, further comprising determining a joint line for the current bone and implant model using said orientation data.

7. The system according to claim 4, further comprising identifying at least one bone axis for the current bone and implant model using said orientation data.

8. The system according to claim 7, wherein identifying at least one bone axis for the current bone and implant model using said orientation data includes identifying the mechanical axis of the bone.

9. The system according to claim 4, wherein obtaining at least one axis of implanted implant includes obtaining the mechanical axis of the bone.

10. The system according to claim 1, wherein the at least one image of at least part of a bone includes two or more radiographic images of the bone, and wherein obtaining at least one image of at least part of a bone includes generating a 3D bone model from the two or more radiographic images of the bone.

11. The system according to claim 1, wherein obtaining a virtual model of the implanted implant using an identity of the implanted implant includes generating a 3D model of the implanted implant from the at least one image, and comparing dimensions of 3D model of the implanted implant to a database of implant geometries to recognize the identity of the implanted implant.

12. The system according to claim 1, wherein obtaining a virtual model of the implanted implant using an identity of the implanted implant includes obtaining a 3D CAD model of the implanted implant.

13. The system according to claim 1, wherein generating and outputting a current bone and implant model includes generating a model of a tibia with implanted implant at a knee and/or of a femur with implanted implant at the knee.

14. The system according to claim 1, wherein guiding alterations in the bone using the current bone and implant model includes guiding a robotic arm using the current bone and implant model.

* * * * *